United States Patent [19]

Motarjemi

[11] Patent Number: 4,588,582

[45] Date of Patent: May 13, 1986

[54] TOOTHPASTE WITH ENTRAINED GAS

[75] Inventor: Minoo Motarjemi, Wirral, England

[73] Assignee: Lever Brothers Company, New York, N.Y.

[21] Appl. No.: 654,920

[22] Filed: Sep. 27, 1984

[30] Foreign Application Priority Data

Sep. 28, 1983 [GB] United Kingdom ................ 8325954

[51] Int. Cl.$^4$ .............................................. A61K 9/16
[52] U.S. Cl. ...................................................... 424/49
[58] Field of Search ..................................... 424/49–58

[56] References Cited

U.S. PATENT DOCUMENTS

| | | | |
|---|---|---|---|
| 3,538,230 | 11/1970 | Pader et al. | 424/50 |
| 3,840,657 | 10/1974 | Norfleet | 424/49 |
| 3,906,090 | 9/1975 | Colodney | 424/49 |
| 3,927,202 | 12/1975 | Harvey et al. | 424/49 |
| 3,944,661 | 3/1976 | Colodney et al. | 424/49 |
| 3,946,108 | 3/1976 | Tomlinson et al. | 424/49 |
| 4,020,154 | 4/1977 | Perla et al. | 424/49 |
| 4,036,949 | 7/1977 | Colodney | 424/49 |

FOREIGN PATENT DOCUMENTS

| | | |
|---|---|---|
| 48590 | 3/1982 | European Pat. Off. . |
| 1304090 | 1/1973 | United Kingdom . |

*Primary Examiner*—Shep K. Rose
*Attorney, Agent, or Firm*—Milton L. Honig; James J. Farrell

[57] ABSTRACT

The appearance of a toothpaste, is modified by incorporating therein 10% to 20% of a gas, the percentage being defined by the ratio of the reduction in density of the aerated paste compared to the density of the non-aerated paste divided by the density of the non-aerated paste, the gas being entrained as discrete bubbles having a diameter within the range 10 to 30 micron to give stability.

3 Claims, 1 Drawing Figure

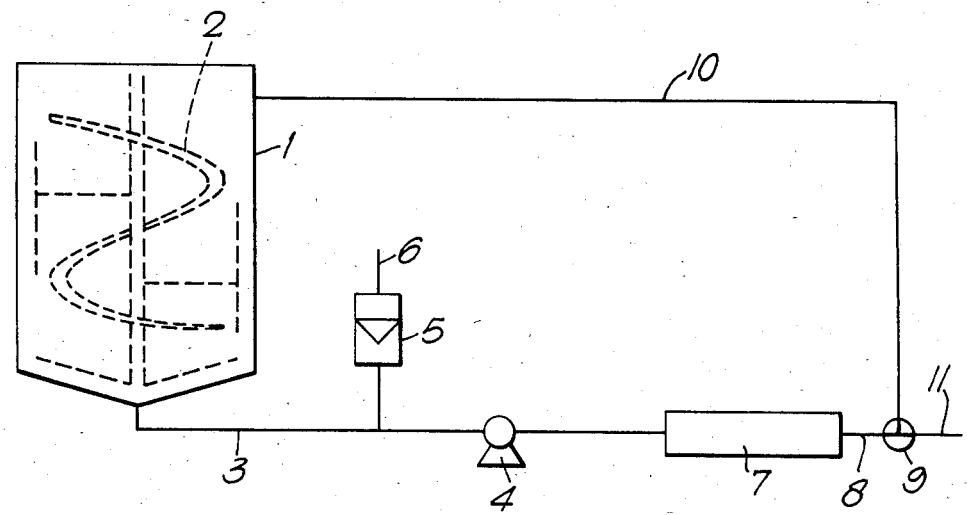

TOOTHPASTE WITH ENTRAINED GAS

This invention relates to the entrainment of gases and particularly to the entrainment of air in toothpaste.

Entrainment of air in a toothpaste can enhance certain properties and particularly the appearance of a toothpaste extruded as a ribbon from a container. For example, incorporating around 5% of air in an opaque toothpaste where the percentage of air included is defined by the expression $$\frac{\text{density of nonaerated paste} - \text{density of aerated paste}}{\text{density of nonaerated paste}} \times 100$$

effect a change in the appearance of the toothpaste giving it a slightly fluffy appearance. Previous attempts to entrain between 10% and 20% air in a toothpaste packaged in a squeeze to use container have not proved successful in that the aerated paste was lacking in the stability necessary to give an adequate shelf life. It was found that within one week the appearance of toothpaste extruded from a container was impaired by the presence of large bubbles of air visible as imperfections on the surface of the extruded ribbon due to bubble disproportionation during storage.

According to the present invention there is provided a toothpaste containing between 10 and 20% gas, the gas being incorporated as discrete bubbles having a diameter within the range 10 to 30 micron. By providing the size distribution of the gas bubbles within a relatively narrow range the rate of bubble dis- proportionation is substantially reduced leading to increased stability of the packaged toothpaste. Thus the appearance of the paste remains substantially the same and the percentage of gas contained within the paste stays almost constant over periods of several nonths. Incorporating more than 20% gas however leads to lack of stability due to the proximity of individual gas bubbles and hence more rapid bubble disproportionation.

Conveniently the gas can be air and the bubble size is preferably between 10 and 20 micron for long term stability.

The toothpaste can be opaque toothpaste aeration of which results in a paste with a richer more creamy appearance than the non-aerated paste, or a transparent toothpaste aeration of which provides a pearlescent or metallised appearance.

Gas can be entrained in a toothpaste in the desired quantities and bubble sizes by passing the material in admixture with the gas through a mixing device of the cavity-transfer type having two closely spaced mutually displaceable surfaces each having a pattern of cavities which overlap during movement of the surfaces so that material moved between the surfaces traces a path through cavities alternately in each surface so that the bulk of the material passes through the shear zone in the material generated by displacement of the surfaces. One such mixer is described in European patent publication No. 0048590A.

The invention will now be described with reference to the accompanying diagrammatic drawing showing a plant layout for entraining air in a toothpaste.

A fully formulated toothpaste is contained within a holding vessel 1 within which it can be subjected to low shear mixing by a stirrer 2. The vessel has an outlet line 3 connecting the bottom of the vessel to a pump 4. Between the holding vessel 1 and pump 4 a rotameter 5 is located in the line 3 through which measured quantities of air can be introduced into the line from inlet 6. The toothpaste is pumped from pump 4 into a cavity transfer mixer 7 and out along line 8. A two way valve 9 in the line 8 can be adjusted to return material leaving the mixer 7 along line 10 to the holding vessel or along line 11 from which the material can be collected.

EXAMPLE 1

A plant layout as shown in the drawing was used with a cavity transfer mixer as described in European patent publication No. 0048590A. The cavity transfer mixer had an inner rotor 5.2 cm in diameter with an effective length of 11.4 cm. The gap between the rotor and the stator was 250 micron and the rotor speed was 300 rpm. Air was entrained in an opaque toothpaste having a formulation based upon 50 parts by weight of aluminium abrasive, 27 parts by weight of 70% sorbital solution and minor amounts of gum, whitener, flavour etc. The toothpaste was passed three times through the mixer and returned to the holding vessel until the desired amount of air was entrained within the toothpaste before being collected from line 11.

A sample of toothpaste was examined after collection and found from photomicrographs to have air present in bubbles of between 20 and 30 micron diameter. The percentage of air incorporated into the toothpaste defined as $$\frac{\text{density of nonaerated paste} - \text{density of aerated paste}}{\text{density of nonaerated paste}} \times 100$$

was determined as 11.2%.

A quantity of the toothpaste was packed into squeeze to use containers and closed in the usual way before being stored at ambient conditions. Samples of the stored paste were examined at intervals for appearance and percentage of entrained air. After one month the percentage of air was unchanged at 11.2% dropping to 11.0% after 1½ months and remaining constant at this level at three months. The stability of the toothpaste in terms of bubble disproportionation was also apparent from the substantially unchanged appearance of a ribbon of toothpaste extruded from a container after three months storage compared with that of the paste before storage.

It was found that the viscosity of the opaque toothpaste increased after aeration resulting in a toothpaste with a richer more creamy appearance than the nonaerated toothpaste. A definite increase in viscosity was observed when the bubble size was below 30 micron. In this case the bubbles are believed to act as solid spheres to increase the solid phase volume and thus increase in the paste viscosity.

EXAMPLE 2

The procedure and plant of Example 1 was used to aerate a transparent toothpaste as described in U.S. patent specification No. 3,538,230. The paste was passed once through the cavity transfer mixer and collected from line 11.

Examination of the toothpaste showed that it contained 16% air and the majority of gas bubbles were in the narrow range of 25 to 35 micron but with a very few larger bubbles.

On storage in squeeze to use containers as before the percentage of air entrained in the paste dropped after one month to 13.6% and after 1½ months to 12.7% and remained at that level after 3 months. It was found however that the few large bubbles increased in size due to bubble disproportionation during storage and these bubbles of air were displaced from the paste and impaired the uniform appearance of the paste.

The presence of the entrained air gave the transparent toothpaste a pearlescent or metallised appearance which remained after the toothpaste had been stored for three months although some disproportionation of the bubbles in the 25 to 35 micron range resulted in a reduction in the pearlescent effect.

EXAMPLE 3

The plant layout of the drawing was used with an Ystral high shear dynamic mixer in place of the cavity transfer mixer. The toothpaste used was the same as in Example 1 and after aeration was found to contain 15.2% air and the bubble size was in the range 10 to 100 micron with a mean diameter of 50 microns. After only 14 days the entrained air in the paste had dropped to 12.7% and after 1 year had fallen to 10.1%. Bubble growth due to disproportionation during the first two weeks of storage was observed from the presence of large bubbles visible in the paste impairing the appearance as compared to the rich and creamy appearance of the freshly aerated toothpaste.

Thus although the aerated toothpastes of Examples 2 and 3 contained some gas bubbles within the range of 10 to 30 micron diameter the toothpastes were unstable compared with that of Example 1 in which the particle size distribution was within this range.

I claim:

1. A transparent or opaque toothpaste whose appearance is stabilized against impaired uniform appearance due to larger bubble disproportionation during storage containing between 10% and 20% entrained air or other gas, the gas being incorporated as discrete bubbles having a diameter within the range 10 to 30 micron and giving the transparent toothpaste a pearlescent or metallized appearance which remains after three months storage of the toothpaste, while giving an opaque toothpaste increased viscosity and a richer, more creamy appearance than a non-aerated toothpaste.

2. A toothpaste according to claim 1 in which the gas is air.

3. A toothpaste according to claim 2, in which the bubble size is between 10 to 20 micron.

* * * * *